(12) United States Patent
Hübner et al.

(10) Patent No.: US 9,796,744 B2
(45) Date of Patent: Oct. 24, 2017

(54) ENTEROCOCCUS FAECALIS AND/OR ENTEROCOCCUS FAECIUM ANTIGEN

(75) Inventors: Johannes Hübner, Freiburg (DE); Otto Holst, Bad Oldesloe (DE); Christian Theilacker, Freiburg (DE); Zbigniew Kaczynski, Gdansk (PL)

(73) Assignee: UNIVERSITÄTSKLINIKUM FREIBURG, Freiburg (DE)

( * ) Notice: Subject to any disclaimer, the term of this patent is extended or adjusted under 35 U.S.C. 154(b) by 683 days.

(21) Appl. No.: 12/514,653

(22) PCT Filed: Nov. 13, 2007

(86) PCT No.: PCT/EP2007/009813
§ 371 (c)(1),
(2), (4) Date: Jun. 17, 2009

(87) PCT Pub. No.: WO2008/058706
PCT Pub. Date: May 22, 2008

(65) Prior Publication Data
US 2010/0055112 A1  Mar. 4, 2010

(30) Foreign Application Priority Data
Nov. 13, 2006  (DE) .................. 10 2006 053 385

(51) Int. Cl.
C07H 15/04 (2006.01)
A61K 39/09 (2006.01)
A61K 39/07 (2006.01)
C08B 37/00 (2006.01)
G01N 33/569 (2006.01)

(52) U.S. Cl.
CPC ............ *C07H 15/04* (2013.01); *A61K 39/07* (2013.01); *C08B 37/006* (2013.01); *G01N 33/56944* (2013.01); *G01N 2333/315* (2013.01)

(58) Field of Classification Search
None
See application file for complete search history.

(56) References Cited

U.S. PATENT DOCUMENTS 6,248,363 B1 *  6/2001  Patel .................... A61K 9/1617
424/422

FOREIGN PATENT DOCUMENTS

WO    WO9908705 A1    2/1999

OTHER PUBLICATIONS

Hedros et al., J. Am. Chem. Soc., 2006; 128: 3414-3419.*
Butler, Methods, 2000; 22: 4-23.*
Goddard et al., Trends in Biotechnology, 2004; 22(7): 363-370.*
Hufnagel et al. 2004 (Serological and Genetic Diversity of Capsular Polysaccharides in Enterococcus faecalis; J Clin Microb 42(6):2548-2557; of record).*
Carolyn T. Hsu, et al., Immunochemical characterization of polysaccharide antigens from six clinical strains of Enterococci, BMC Microbiology, Jul. 12, 2006, vol. 6, No. 62, Publisher: BioMed Central Ltd., Published in: United States.
Marcus Hufnagel, et al., Serological and Genetic Diversity of Capsular Polysaccharides in *Enterococcus Faecalis*, Journal of Clinical Microbiology, Jun. 2004, pp. 2548-2557, vol. 42, No. 6, Publisher: American Society for Microbiology, Published in: United States.
Christian Theilacker, et al., Opsonic Antibodies to Enterococcus Faecalis Strain 12030 Are Directed against Lipoteichoic Acid, Infection and Immunity. Oct. 2006, pp. 5703-5712, vol. 74, No. 10, Publisher: American Society for Microbiology, Published in: United States.
International Preliminary Report on Patentability from PCT/EP2007/009813.
Office Action in German Patent Application Serial No. 10 2006 053 385.2 dated Jun. 26, 2007.
Office Action in Canadian Patent Application No. 2,669,237 dated Apr. 25, 2013.
Office Action in Australian Patent Application No. 2007321400 dated Oct. 6, 2011.
Hufnagel et al., "Distribution of Four Capsular Serotypes of *Enterococcus faecalis* among Clinical Isolates from Different Geographical Origins and Infection Sites", Infection, vol. 34, No. 1, pp. 22-25 (2006).
Hufnagel et al., "Naturally Acquired Antibodies Against Four *Enterococcus faecalis* capsular Polysacharides in Healthy Human Sera", Clinical and Diagnostic Laboratory Immunology, vol. 12, No. 8, pp. 930-934 (2005).
Beynon et al., "Identification of the common antigenic determinant shared by *Streptococcus pneumoniae* serotype 35A capsular polysaccharide", Eur. J. Biochem, vol. 250, pp. 163-167 (1997).
Beynon et al., "Characterization of the capsular antigen of *Streptococcus pneumoniae* serotype 35B", Can J. Chem., vol. 73, No. 41 pp. 41-48 (1995).

* cited by examiner

Primary Examiner — Gary Nickol
Assistant Examiner — Mary Lyons
(74) Attorney, Agent, or Firm — Saliwanchik, Lloyd & Eisenschenk

(57) ABSTRACT

The present invention generally relates to the field of detecting and preventing infectious diseases caused by *Enterococcus faecalis* and/or *Enterococcus faecium*. More specifically, the invention relates to an *Enterococcus faecalis* and/or *Enterococcus faecium* antigen which comprises at least one unit having the following general formula:

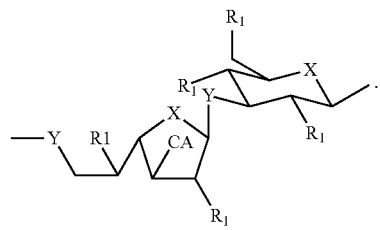

9 Claims, 7 Drawing Sheets

ENTEROCOCCUS FAECALIS AND/OR ENTEROCOCCUS FAECIUM ANTIGEN

CROSS REFERENCE TO RELATED APPLICATIONS

This application is a national stage application of International Application No. PCT/EP2007/009813, filed 13 Nov. 2007, which claims the benefit of German Patent Application Serial No. 10 2006 053 385.2, filed 13 Nov. 2006 from which applications priority is claimed.

The present invention generally relates to the field of detecting and preventing infectious diseases caused by *Enterococcus faecalis* and/or *Enterococcus faecium*.

More specifically, the present invention relates to an antigen, antibodies, compositions, methods, a kit, and to a use.

Nosocomial infections (hospital-acquired infections) are infections which are caused by microorganisms and which are causally linked to hospitalization.

The proportion of nosocomial infections increased by 36% in the USA from 1975-1995 so that, in 1995, about 10 of 1000 patients were affected by such an infection.

Thus, nosocomial infections alone are responsible for 44 000-98 000 deaths per annum in the USA.

Hospital-acquired infections are responsible for a large part of all hospital-based complications, and avoiding them is essential for the quality of medical care and nursing of the patients.

They are therefore a serious problem for any hospital, since the supreme aim of any quality-oriented actions in hospital care is of course a healthy patient.

Nosocomial infections not only put a strain on the patient himself due to additional pain, but usually also prolong hospitalization—on average by about 4 days—and therefore contribute to hospitals and the health-care system being overburdened. Nosocomial infections produce costs of from 17 to 29 billion US dollars per year in the USA.

Despite indisputable medical progress, the frequency of nosocomial infections is expected rather to increase in the future.

The following factors are inter alia held responsible for this development:
the number of elderly patients increases,
an increasing number of patients whose endogenous infection defenses are weak are treated in the hospitals,
more complicated and difficult operations are carried out owing to the progress in surgical technologies,
it is increasingly possible to carry out invasive measures involving complicated apparatus and having an increased risk of infection,
therapeutic measures which lower the defenses are increasingly carried out, and
antibiotics, in particular broad-spectrum antibiotics, are increasingly employed, resulting in an increase in multiresistant microorganisms.

More recent studies carried out in this connection (Am. J. Infect. Control., 32:470-485, 2004) have demonstrated that up to 25% of *Enterococcus faecium* isolates from hospitals are resistant to glycopeptidic antibiotics.

Glycopeptidic antibiotics attack the cell wall and insert directly into the structure of the cell wall, thereby producing holes and enabling water to enter. An example of glycopeptidic antibiotics is vancomycin.

DiazGranados, C. A., et al. recently demonstrated that vancomycin-resistant enterococci cause considerable morbidity and mortality, in particular in patients whose immune system has already been weakened (Clin. Infect. Dis., 41:327-333, 2005).

There is therefore continuing interest in developing immunotherapeutic approaches which allow such infections to be prevented or at least controlled.

Although the use of carbohydrate antigens in the development of vaccines is known in the prior art in principle (Ada, G., et al., Clin. Microbiol. Infect., 9: 79-85, 2003), little is known up to now about cell wall-associated and capsular polysaccharides in *Enterococcus faecalis*.

Four carbohydrate antigens have been described up to now (Hancock, et al., Proc. Natl. Acad. Sci. USA, 99:1574-1579, 2002; Hsu et al., BMC Microbiol., 6:62, 2006; Pazur et al., J. Biol. Chem., 248: 279-284, 1973; Wang et al., Carbohydr. Res. 316: 155-160, 1999; Xu et al., Infect. Immun., 65:4207-4215, 1997; Xu et al., Infect. Immun. 66:4313-4323, 1998; Xu et al., Infect. Immun., 68:815-823, 2000), however, a complete structural analysis has been carried out only for one of them. A carbohydrate antigen which is exposed on the cell surface of the *Enterococcus faecalis* strain FA2-2 and which consists of glucose, galactose and glycerol phosphate has also been described.

In order to solve the problems caused by the appearance of multiresistant *Enterococcus faecalis* strains and the closely related *Enterococcus faecium* strains, there is a considerable need in the prior art for characterizing antigens exposed on the surface of *Enterococcus faecalis* and/or *Enterococcus faecium*, in order to use said antigens for overcoming the problems described above.

It is therefore the object of the present invention to provide previously unknown antigens of *Enterococcus faecalis* and/or *Enterococcus faecium*.

Another object of the present invention is to provide antibodies to these previously unknown antigens of *Enterococcus faecalis* and/or *Enterococcus faecium*.

Another object of the present invention is to provide a composition which comprises at least one antigen of *Enterococcus faecalis* and/or *Enterococcus faecium* or an antibody thereto, which composition is preferably suitable for active or passive immunization against *Enterococcus faecalis* and/or *Enterococcus faecium* infections.

Another object of the present invention is to provide a method which enables the previously unknown antigen to be detected in a sample.

Another object of the present invention is to provide a method which enables antibodies to the previously unknown antigen to be detected in a sample.

Another object of the present invention is to provide a kit which enables the previously unknown antigen or antibodies to this antigen to be detected.

Another object of the present invention is to provide a possible use of the previously unknown antigen for detecting or producing corresponding antibodies or antibody fragments and to provide a corresponding method.

These objects of the present invention are achieved by the antigen, by the antibodies, by the compositions, by the methods, by a kit, and by a use.

More specifically, the present invention provides an *Enterococcus faecalis* and/or *Enterococcus faecium* antigen which is characterized in that it comprises at least one unit having the following general formula:

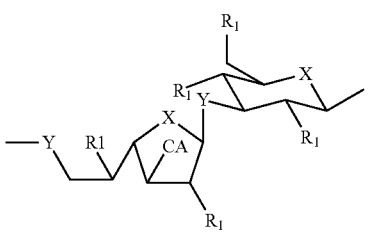

wherein $R_1$ are independently of one another selected from the group consisting of H, OH, $OCH_3$, OAc, $OC_nH_m$, OFo, OAcyl, SH, $SCH_3$, $SC_nH_m$, SFo, SAc, SAcyl, $NH_2$, $NHCH_3$, $NHC_nH_m$, NHFo, NHAc, NHAcyl, $PO_2(OR_2)_2$, F, Cl, Br and I, wherein Fo is formyl, $R_2$ is independently selected from the group consisting of H, $C_nH_m$, $C_nH_{m-1}NHR^3$ and $C_nH_{m-1}N(CH_3)_3$, wherein $R_3$ is independently selected from the group consisting of H, Fo, Ac and acyl, X are independently of one another selected from the group consisting of O, S, $CH_2$, NH and $POOR_4$, wherein $R_4$ is H, $C_nH_m$, $C_nH_{m-1}NHR^3$ and $C_nH_{m-1}N(CH_3)_3$, Y are independently of one another selected from the group consisting of O, S, $CH_2$ and $HPO_4$, CA is independently of one another selected from the group consisting of $C_1$-$C_6$-acyl radicals, in particular hydroxyacyl radicals, preferably lactyl, H, OH, $OCH_3$, OAc, $OC_nH_m$, OFo, OAcyl, SH, $SCH_3$, $SC_nH_m$, SFo, SAc, SAcyl, $NH_2$, $NHCH_3$, $NHC_nH_m$, NHFo, NHAc, NHAcyl, $PO_2OR^2$, F, Cl, Br and I, wherein Fo is formyl, $R_2$ is independently selected from the group consisting of H, $OC_nH_m$, $OC_nH_{m-1}NHR^3$ and $OC_nH_{m-1}N(CH_3)_3$, wherein $R_3$ is independently selected from the group consisting of H, Fo, Ac and acyl, wherein m=2n+1 and n is selected from the set of natural numbers from 1 to 10.

The two sugars in this unit are preferably in the D configuration.

Particular preference is given to the antigen of the present invention, characterized in that the disaccharide consisting of a furanose Gal and a pyranose Glc has a structure which is selected from the following:

→-v)-D-Galf-(1→-z)-D-Glcp-(1→-,
→-z)-D-Galf-(1→-z)-D-Glcf-(1→-,
→-v)-D-Galp-(1→-z)-D-Glcp-(1→- or
→-v)-D-Galp-(1→-z)-D-Glcf-(1→-, wherein v and z are in each case 1, 2, 3, 4, 5 or 6.

An antigen particularly preferred in accordance with the present invention has the following formula:

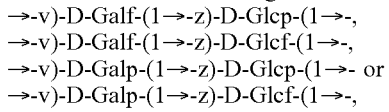

Further preference is given to $R_1$ being OH, X being O, Y being O and CA being lactyl.

The molecular weight of the antigens of the present invention is noncritical in principle and is therefore not restricted any further. Typically, however, the antigens of the present invention have molecular weights of approx. 1000-200 000 Da, more preferably of approx. 50 000-150 000 Da, particularly preferably of approx. 100 000 Da. Molecular weights which are too small may possibly result in the antigen not being able to form any structurally stable epitopes, due to the few intramolecular interactions, while molecular weights which are too high result in such antigens frequently being difficult to synthesize and their lifetime being limited.

It is sufficient in principle for the antigen of the present invention to include the unit of claim 1 at least once. It is however possible to increase the antigenicity of the antigen of the present invention by said unit occurring at least 5 times, preferably at least 10 times, more preferably at least 100 times, particularly preferably at least 1000 times, per antigen.

For various analytical applications of the antigen of the present invention, preference may further be given to said antigen being immobilized. This may restrict the presence of the antigen locally, so that many different samples are contacted with the antibody and analyzed simultaneously but nevertheless separately, for example within the framework of an array. Immobilized antigens are also useful in affinity-based purification methods, for example for corresponding antibodies.

Therefore, in a preferred embodiment of the invention, the antigen is bound to a support, preferably to an immunosupport.

Immobilization may be carried out in principle by any type of interactions, such as, for example, van der Waals forces, ionic interactions, dipole-dipole interactions, hydrogen bonding or hydrophobic interactions. Preference is given, however, to the binding to the support being of the covalent type.

Preference is given to the antigen of the present invention being provided in the form of a composition. According to a preferred embodiment, such a composition comprises at least one pharmaceutically acceptable support. A support substance here is any substance to which the antigen can be added on and/or physically bound. Thus it is possible, for example, for the antigen whose dose can usually be administered only with difficulty to be bound to a support whose dose can be administered more easily. Examples of such supports are starch and maltodextrin. Pharmaceutically acceptable here means that the support used is nontoxic and does not interfere with the action of the antigen.

The antigen of the present invention may be administered as a preventive measure to a patient within the framework of an active vaccination against infectious diseases caused by *Enterococcus faecalis* and/or *Enterococcus faecium*. The aim of such a vaccination is to stimulate the endogenous immune system itself to form specific antibodies, thereby producing a specific immunity to *Enterococcus faecalis* and/or *Enterococcus faecium*. A patient may therefore be any living being that has an immune system. Of particular importance, however, are mammals such as, for example, humans, nonhuman primates, dogs, cats, pigs, cows, horses, goats and sheep, and birds such as, for example, chickens, ducks, geese, turkeys or ostriches.

In this respect, the antigen of the present invention, in a preferred embodiment, is a vaccine against *Enterococcus faecalis* and/or *Enterococcus faecium*.

The present invention likewise relates to an antibody to the above-described antigen.

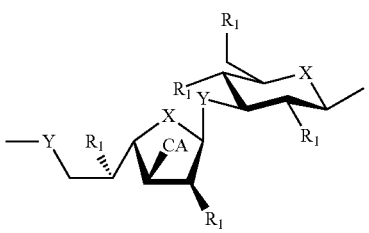

This antibody may be a monoclonal or a polyclonal antibody.

Antibodies consist of two identical heavy chains (H) and two identical light chains (L), which are linked to one another by covalent disulfide bonds to give a Y-shaped structure. Depending on the organism and immunoglobulin subclass, the two light chains are either of the kappa type or of the lambda type and, together with the heavy chain portion located upstream of the hinge region, form the antigen-binding fragment, Fab, which can be removed enzymatically from the downstream crystalline fragment, Fc.

The marked variability of the antibody bonding sites (abbreviated CDR, Complementarity Determining Region) is achieved by the organism via V(D)J recombination.

The light chains consist in each case of a variable and a constant domain. These are referred to as $V_L$ and $C_L$. The heavy chains, in contrast, have in each case one variable and three constant domains. These are referred to analogously as $V_H$ and $C_H1$, $C_H2$, $C_H3$.

Antibodies in accordance with the present invention are whole antibodies or fragments thereof, for example Fab or scFv, provided that the latter are capable of binding to the antigen, at least to a limited extent.

The present invention likewise comprises humanized and chimeric antibodies.

An antibody of this kind and/or the antigen of the present invention may be employed, for example, within the framework of

- an ELISA method of quantifying antigens or antibodies, for example in the serum, in cell culture supernatant, etc., by means of enzyme-coupled antibodies,
- an ELISPOT method of detecting antibody- or antigen-secreting cells (plasma cells) by means of enzyme-coupled antibodies,
- an FACS method of quantifying cells by means of fluorescently coupled antibodies to antigens on the cell surface, in the zytoplasm or in the nucleus,
- a Western blot,
- a super gel shift experiment (also EMSA),
- a phage display,
- a drugwipe assay,
- an abzyme method, or
- a method of purifying the antigens or antibodies of the present invention by appropriate affinity methods.

The antibody of the present invention, like the antigen, is preferably provided within the framework of a composition which in turn—like the antigen—preferably comprises a pharmaceutically acceptable support.

The antibody of the present invention is used within the framework of a particularly preferred embodiment of the present invention for passive vaccination against *Enterococcus faecalis* and/or *Enterococcus faecium* and thus represents a vaccine against *Enterococcus faecalis* and/or *Enterococcus faecium*.

Passive vaccination involves vaccination with a vaccine serum which includes, preferably high concentrations of, the specific antibody of the present invention to *Enterococcus faecalis* and/or *Enterococcus faecium*.

Preference is given in principle to the compositions of the present invention being pharmaceutical compositions. These are distinguished in that they are suitable for administration within the framework of a therapy or prophylaxis.

The present invention further relates to a method of detecting *Enterococcus faecalis* and/or *Enterococcus faecium* antibodies, said method comprising the following steps:

contacting antigens according to the present invention with a sample to be tested for *Enterococcus faecalis* and/or *Enterococcus faecium* antibodies, and detecting antibody-antigen or antibody-antigen conjugate complexes, wherein the presence of such complexes indicates the presence of *Enterococcus faecalis* and/or *Enterococcus faecium* antibodies in the sample.

The present invention likewise comprises a method of detecting *Enterococcus faecalis* and/or *Enterococcus faecium* antigens, having at least the following steps:

contacting antibodies according to the present invention, optionally immobilized on a support, with a sample to be tested for *Enterococcus faecalis* and/or *Enterococcus faecium* antigens, and detecting antigen-antibody or antibody conjugate-antigen complexes, wherein the presence of such complexes indicates the presence of *Enterococcus faecalis* and/or *Enterococcus faecium* antigens in the sample.

In the two methods above, preference is given to the antigens or antibodies being immobilized on a matrix, in particular on a solid matrix, preferably on a microtiter plate.

As an alternative, it is also conceivable for the sample to be examined to be immobilized to a matrix.

In each case, detection of antigen-antibody conjugates formed is particularly facilitated, since unbound sample components can optionally be removed from the matrix, for example by washing, prior to detecting the complexes. This reduces noise and increases measurement accuracy, and the use of a solid matrix also facilitates handling of the samples by machine, and, as a result, the method of the present invention has, inter alia, excellent suitability for automation and thus, for example, for high throughput screening.

Detection of the antigen-antibody conjugates may further be facilitated by providing the antigen or the antibodies of the present invention with a detectable marker.

If, for example, the sample to be examined, which may contain anti-*Enterococcus faecalis* and/or *Enterococcus faecium* antibodies, has been immobilized on a matrix and if this immobilized sample is then contacted with labeled antigens of the invention, then samples containing anti-*Enterococcus faecalis* and/or *Enterococcus faecium* antibodies, after washing, may already be recognized by way of the signal released by the marker on the antigen.

A suitable compound which can be used as marker is any compound that can be contacted with the antibodies or antigens of the present invention, without said contact totally interrupting the antigen-antibody interactions, and which generate a detectable signal of any kind directly or indirectly, where appropriate after appropriate activation or introduction of substrate.

Preferred markers in accordance with the present invention are radioactive markers, colored markers, enzymatic markers and magnetic markers.

The detection method of the present invention may be accelerated further if the marker displays a property change after binding to an antibody or to an antigen. This would enable unbound labeled antigens, or antibodies, to be distinguished from bound ones without the need for a washing step, for example.

The present invention likewise provides for a kit for detecting *Enterococcus faecalis* and/or *Enterococcus faecium* antibodies and/or *Enterococcus faecalis* and/or *Enterococcus faecium* antigens, which kit comprises the antigen and/or the antibody of the present invention in any of the embodiments described above.

More specifically, the antigen of the invention and/or the antibody of the invention may be bound to a support, preferably to a solid matrix, and/or labeled with a marker, preferably a radioactive marker, a colored marker, an enzymatic marker or a magnetic marker.

The present invention furthermore comprises the use of the antigen of the invention according to claims 1 to 10 for detecting or producing *Enterococcus faecalis* and/or *Enterococcus faecium* antibodies and/or antibody fragments, in particular Fab or scFv.

The *Enterococcus faecalis* and/or *Enterococcus faecium* antibodies and/or antibody fragments produced in this way are designed in particular for passive immunotherapy or for prophylaxis against *Enterococcus* antigens.

The antibodies or antibody fragments of the invention, in particular Fab or scFv, can be prepared, for example, by a method which comprises administering the antigen of the invention to an animal, in particular a mammal, in an amount sufficient for producing antibodies or antibody fragments.

Polyclonal antibodies of the present invention may be prepared by firstly selecting and producing the antigen of the invention to which the antibody is intended to be directed. This may be achieved in various ways, for example by isolating an antigen from *Enterococcus faecalis* and/or *Enterococcus faecium* synthesizing said antigen in vitro or producing it recombinantly, for example in bacteria. The antigen is then administered to an animal whose immune system then forms antibodies to the antigen. Suitable antibody producers are in particular mice, rats and rabbits but also goats, sheep and horses. Preference is given to repeating the immunization several times. After a few weeks, polyclonal antibodies are taken from the blood or the serum of the antibody producer.

Monoclonal antibodies may be produced—as described for production of polyclonal antibodies—by immunizing animals, preferably mice and/or rats, and then obtaining their plasma cells (from spleen or lymph nodes). These plasma cells may be fused with tumor cell lines, thereby enabling "hybridoma cell lines" to be generated which, in theory, live forever but secrete a single type of monoclonal antibodies which in turn may be isolated from the cell culture supernatant.

Another embodiment of the present invention is a method of producing an antibody of the invention or a fragment thereof, in particular Fab or scFv, in recombinant form, which method comprises cloning a DNA sequence which codes for said antibody or its fragment into an expression vector, transforming a cell, in particular an *E. coli* cell or a yeast cell or a eukaryotic cell (such as, for example, a CHO cell), with this construct and expressing the recombinant antibody or a fragment thereof.

A recombinant antibody obtainable by such a method is characterized in that it corresponds structurally to the antibodies of the present invention. In the same way, recombinant fragments of the antibody of the invention, in particular Fab or scFv, correspond to the natively purifiable antibody fragments of the present invention.

The recombinant antibodies and antibody fragments of the present invention have the particular advantage that they can be produced in large quantities without complicated technology and without animals having to be used as antibody producers. It is furthermore possible to achieve a considerably higher purity of the antibody preparations, and direct contact with blood and the risk of infection associated therewith are avoided.

It is obvious to the skilled worker that he can combine all embodiments of the present invention which are listed here by way of example in any way without departing from the scope of the disclosure of the present invention.

Furthermore, reference is made to the entire contents of any citations herein.

Further advantages and embodiments of the invention will be evident from the description of individual exemplary embodiments and from the drawing.

In the figures,

FIG. 1 depicts the $^1$H NMR spectrum of the capsular polysaccharide from *E. faecalis* strain type 5. The spectrum was recorded at 600 MHz and 27° C. The letters refer to the carbohydrate radicals as depicted in FIG. 3, and the Arabic numerals refer to the protons on the corresponding radicals; LA, lactic acid.

FIG. 2 depicts sections of the ROESY spectrum of the capsular polysaccharide from *E. faecalis* strain type 5. The spectrum was recorded at 600 MHz and at 27° C. The letters refer to the carbohydrate radicals as depicted in FIG. 3, and the Arabic numerals refer to the protons on the corresponding radicals. The NOE contacts between the radicals are underlined and depicted in italics.

FIG. 3 depicts the chemical structure of the repetitious unit of the capsular polysaccharide of *E. faecalis* strain type 5. LA, lactic acid. The Galf radical is assumed to have the D configuration.

FIG. 4 depicts binding of a rabbit antiserum to the bacterial cells of *E. faecalis* strain type 5. The antigens used are indicated in the legend. The values indicated represent in each case the average of at least two measurements.

FIG. 5 depicts the inhibition of opsonophagocytosis of *E. faecalis* strain type 5 bacterial cells by rabbit antiserum. All antisera were used as 1:200 dilutions. The inhibitors are indicated in the legend. The data indicated represent an average of at least 4 measured values, and the error bars represent the SEM. The opsonophagocytotic activity without inhibitor was >70% for all antisera.

EXAMPLE 1

Figure 1:
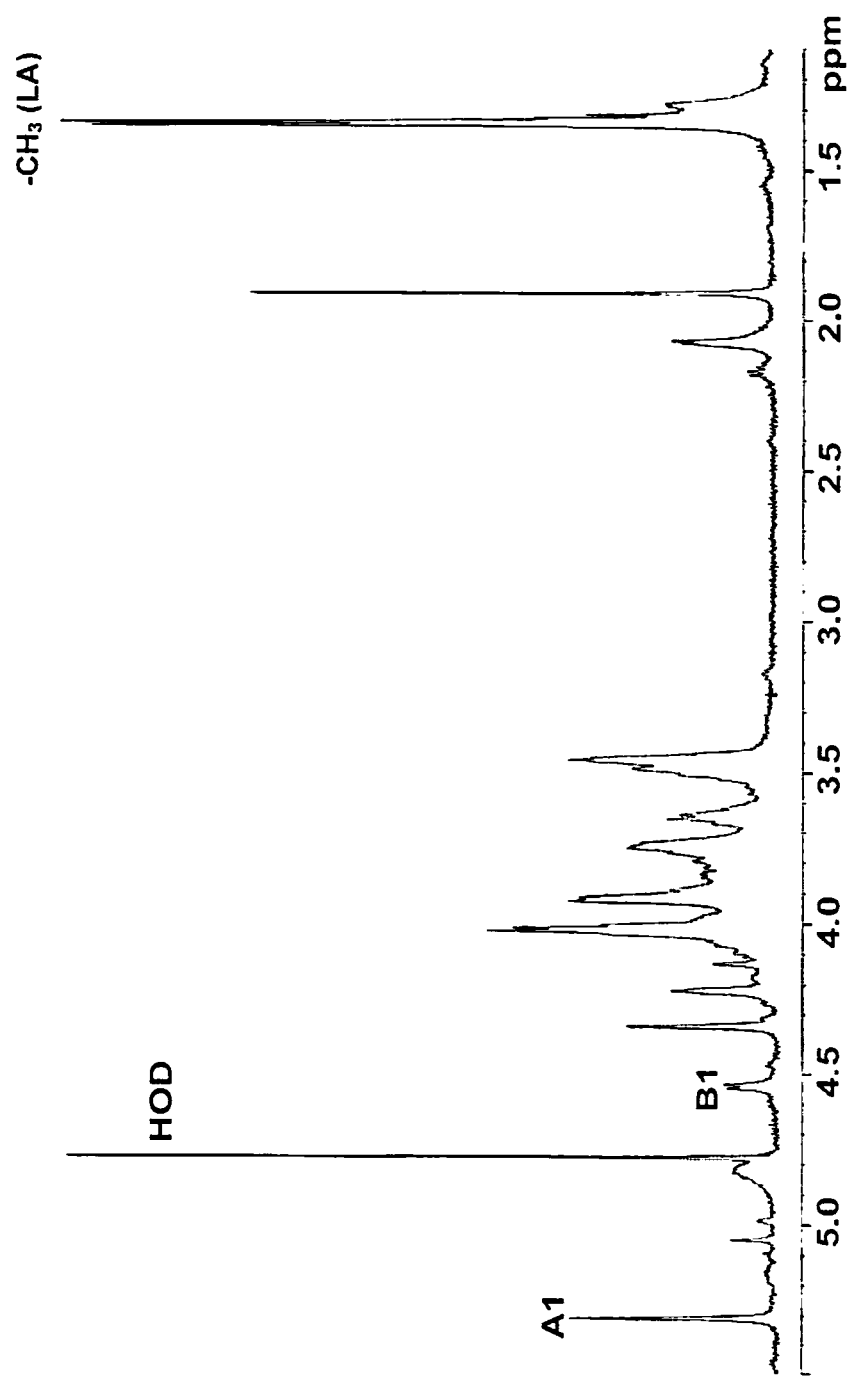

Elimination of *Enterococcus faecalis* by opsonophagocytosis is accomplished inter alia by antibodies which are directed to carbohydrate antigens of the cell wall and of the bacterial capsule. Recently, lipoteichoic acid (LTA) has been identified as target of the opsonizing antibodies in *E. faecalis* strain 12030. However, serum raised against purified LTA does not kill any bacterial strains having the CPS-C and -D serotypes.

The present example comprises isolating a novel capsular polysaccharide from the *E. faecalis* type 5 strain, a CPS-D strain, by enzymatic digestion of the cell wall and by gel permeation and anion exchange chromatography.

The isolated polysaccharide is analyzed by sugar analysis, one-dimensional and two-dimensional homonuclear and heteronuclear $^1$H and $^{13}$C NMR spectroscopy.

A novel *E. faecalis* capsular polysaccharide is identified which includes an unusual →6)-3-O-[1-carboxyethyl]-β-Galf-(1→ unit in the repetitious unit.

A rabbit antiserum induced by means of immunization of heat-inactivated E. faecalis type 5 bacteria cells contained both antibodies specific to the novel capsular polysaccharide and antibodies to LTA of said strain.

However, opsonophagocytosis of E. faecalis type 5 by this antiserum was inhibited only by the purified polysaccharide but not by LTA.

This example therefore illustrates a possibility of how to identify a novel capsular polysaccharide as antigen in E. faecalis type 5 that is immunogenic and can serve as target for opsonizing antibodies.

This example further illustrates how to assay the immunogenicity of antigens derived from E. faecalis.

EXAMPLE 2

2a) Bacteria Strains and Cultures

Capsular polysaccharides were isolated from E. faecalis type 5 (Maekawa, S., et al., Microbiol. Immunol., 36:671-681, 1992) a CPS-D strain, using a recently described serotyping system (Hufnagel, M., et al., J. Clin. Microbiol. 42:2548-2557, 2004). Bacteria cells were cultured from the starter cultures in a Columbia nutrient solution (Becton Dickinson, Sparks, Md., USA) enriched with 1% glucose, without agitation at 37° C. for 2 hours.

2b) Antisera

Antisera to whole bacteria cells of E. faecalis type 5 have been described in the past (Hufnagel, M., et al., J. Clin. Microbiol. 42:2548-2557, 2004). The antiserum to LTA was produced with LTA purified from the strain 12030, as described previously (Theilacker, C., et al., Infect. Immun. 74, 2006). A female white New Zealand rabbit was immunized subcutaneously with 100 µg of LTA suspended in complete Freund's adjuvant, and thereafter with the same LTA dose suspended in incomplete Freund's adjuvant seven days later, and then with 10 µg booster doses every three days in the following week.

2c) Preparation and Characterization of the Capsular Polysaccharide.

E. faecalis LTA was isolated as described previously (Huebner, J., et al., Infect. Immun. 67:1213-1219, 1999; Theilacker, C., et al., Infect. Immun. 74, 2006). The antigen described herein was prepared as follows: briefly, bacterial cells were harvested by centrifugation and digested by adding mutanolysin and lysozyme (in each case 100 pg/ml, Sigma Chemicals, St. Louis, Mo., USA in PBS enriched with 5 mM $MgCl_2$, 1 mM $CaCl_2$ and 0.05% $NaN_3$) at 37° C. for 18 hours. Insoluble material was removed by centrifugation, and the supernatant was treated with nucleases (DNase I and RNase A, 100 pg/ml) at 37° C. for 4 hours, followed by 18 hours of adding proteinase K (100 pg/ml, all available from Sigma Chemicals) at 56° C. The supernatant was precipitated by adding ethanol (final volume 80%) and then collected by centrifugation. After dialysis against deionized $H_2O$, the material was lyophilized. For gel permeation chromatography, the material was dissolved in 0.01 M ammonium bicarbonate buffer solution and applied to a Sephacryl S-400 column (1.6×90 cm) (GE Healthcare, Uppsala, Sweden). Fractions eluting at a $K_{av}$ of about 0.45 were combined, dialyzed and lyophilized. The material was resuspended in 20 mM of $NaHCO_3$, pH 8.4 and applied to an anion exchange column (Sepharose Q FF, GE Healthcare). Bound antigen was eluted from the column by way of a linear NaCl gradient, and fractions comprising polysaccharides were identified by a Dubois assay (Dubios, M., et al., Anal. Chem. 28:350-356, 1956.) and immunoblotting using a rabbit anti-type 5 immune serum. Immunoreactive material eluting at 450 mM NaCl was combined, dialyzed and lyophilized. The final purification step performed was a gel permeation chromatography on a 1.5×75 cm Toyopearl HW-40 (Tosoh Corporation, Tokyo, Japan) column. The purity of the isolated material was confirmed by means of SDS PAGE using a 10% Bis-Tris gel and an MOPS running buffer (Invitrogen, Karlsruhe, Germany) and by Coomassie (Invitrogen) and PAS (Sigma) staining according to the manufacturer's instruction.

Furthermore, a Western blot of material removed by SDS PAGE was stained using an anti-type 5 rabbit antiserum.

2d) Result of the Purification of the Capsular Polysaccharide

Capsular polysaccharide of the E. faecalis strain type 5 was mobilized by enzymatic digestion of peptidoglycan from the bacterial cells. The extracted material eluted in the form of two carbohydrate-containing fractions in Sephacryl S-400 gel chromatography. One fraction eluting in the void volume comprised LTA as determined by $^1H$ NMR analysis (data not shown). A large, second fraction at a $K_{av}$ of around 0.45 was further purified by anion exchange chromatography using Q Sepharose. Small amounts of immunoreactive material eluted at 450 mM NaCl, which material comprised only glucose and galactose, and which was subjected to further analysis after gel permeation chromatography on Toyopearl HW-40S. The SDS PAGE of this purified material showed a single broad band at 100 kDa which was stained by PAS but not by Commassie blue. A Western blot stained with anti-type 5 antiserum likewise showed a single broad band at 100 kDa and no further bands (data not shown).

EXAMPLE 3

Provision of LTA

LTA was prepared by butanol extraction and hydrophobic interaction chromatography as described previously (Theilacker, C., et al., Infect. Immun. 74, 2006). The purity of the LTA preparations was evaluated by SDS PAGE and Western blot analysis using the corresponding antiserum to whole bacterial cells (cf. above). The structural identity of LTA was confirmed by NMR spectroscopy as recently described (Theilacker, C., et al., Infect. Immun. 74, 2006).

General and Analytical Methods

Hydrolysis was carried out using 2 M trifluoroacetic acid (120° C., 3 h). Monosaccharides were converted to alditol acetates and analyzed by GC in a Hewlett-Packard 5890 chromatograph with an SPB-5 column (30 m×0.25 mm×0.25 pm, Supelco, Munich, Germany), using a temperature program of 150° C. for 3 minutes, then 3° C. $min^{-1}$ up to 300° C. The absolute arrangement of the sugar radicals was determined as described previously (Haseley, S. R., et al., Eur. J. Biochem. 244:761-766, 1997; Leontein, K., et al., Carb. Res. 62:359-362, 1978).

NMR Spectroscopy

The sample was substituted three times with 99.0% $^2H_2O$, lyophilized and redispersed in 99.9% $^2H_2O$. All one- and two-dimensional spectra were recorded on a Bruker DRX Advance 600 MHz spectrometer (working frequencies of 600.31 MHz for $^1H$ NMR and 150.96 MHz for $^{13}C$ NMR) using a conventional Bruker Software (Bruker, Rheinstetten, Germany) at 27° C. The chemical shifts are indicated in relation to acetone (δH 2.225; δC 31.45). Correlation spectroscopy (COSY), and total correlation spectroscopy (TOCSY), and ROESY were recorded using datasheets (t1×t2) containing 4096×512 points, and 32 scans were carried out.

TOCSY and ROESY were carried out in a phase-sensitive manner according to the method of States et al., with a mixing time of 100 ms being used for TOCSY (States, D. J., et al., J. Magn. Reson. 48:286-292, 1982). The $^1$H, $^{13}$C correlations were measured in $^1$H detection mode by means of a multiple quantum coherence (HMQC) with proton decoupling in the $^{13}$C domain using datasets containing 2048×256 points, with 128 scans being recorded for each $t_1$ value (Bax, A., et al., J. Am. Chem. Soc. 109:2093-2094, 1986; Summers, M. F., et al., J. Am. Chem. Soc. 108:4285-4294, 1986).

Chemical Analysis and NMR Spectroscopy

In the low field region, the $^1$H NMR spectrum of the purified polysaccharide (FIG. 1) showed two anomeric signals at δ 5.315 (radical A, [$^3J_{H1,H2}$<2 Hz]), and at δ 4.542 (radical B, [$^3J_{H1,H2}$=7.8 Hz]), which were identified as β-Galf and β-D-Glcp. Furthermore, the Dublett at δ 1.361 was identified as a methyl group which belongs to a lactic acid radical (LA) (Knirel, Y. A., et al., Carbohydr. Res. 259, 1994; Knirel, Y. A., et al., Carbohydr. Res. 235:C19-23, 1992). The presence of a D-Glcp radical was confirmed by chemical analysis, assigning of the absolute configuration, and by NMR spectroscopy data. The Galf radical substituted with lactic acid in position C-3 was identified only by NMR data (Beynon, L. M., et al., Eur. J. Biochem. 250:163-167, 1997; Knirel, Y. A., et al., Carbohydr. Res. 259, 1994; Knirel, Y. A., et al., Carbohydr. Res. 235:C19-23, 1992). All $^1$H and $^{13}$C chemical shifts of the capsular polysaccharide of *E. faecalis* type 5 (Table 1) were determined from $^1$H, $^1$H COSY and TOCSY, and from $^1$H, $^{13}$C HMQC spectra.

TABLE 1

| | Chemical shift $^1$H and $^{13}$C [δ] | | | | | | |
|---|---|---|---|---|---|---|---|
| Radical | H1 C1 | H2 C2 | H3 C3 | H4 C4 | H5 C5 | H6$^a$ C6 | H6$^b$ |
| A | 5.315 | 4.346 | 3.932 | 4.225 | 4.040 | 3.768 | 4.019 |
| →6)-β-Galf- | 109.26 | 80.26 | 84.96 | 82.41 | 70.55 | 71.90 | |
| B | 4.542 | 3.460 | 3.663 | 3.465 | 3.500 | 3.742 | 3.930 |
| →3)-β-D-Glcp- | 103.22 | 74.05 | 82.44 | 68.80 | 76.26 | 61.26 | |
| LA | | 4.038 | 1.361 | | | | |
| Lactic acid | 181.29 | 77.72 | 19.21 | | | | |

Figure 2:
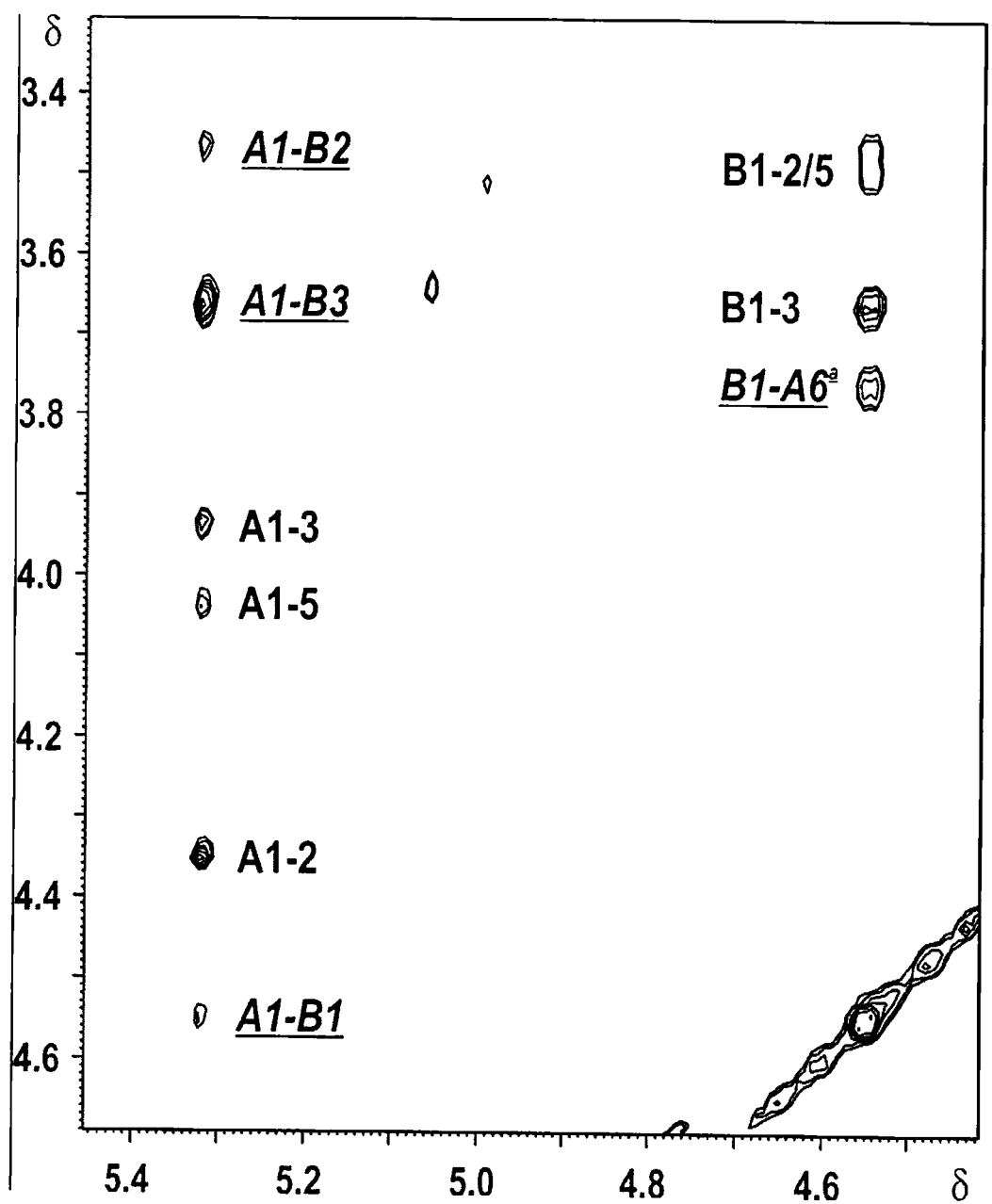
Figure 3:
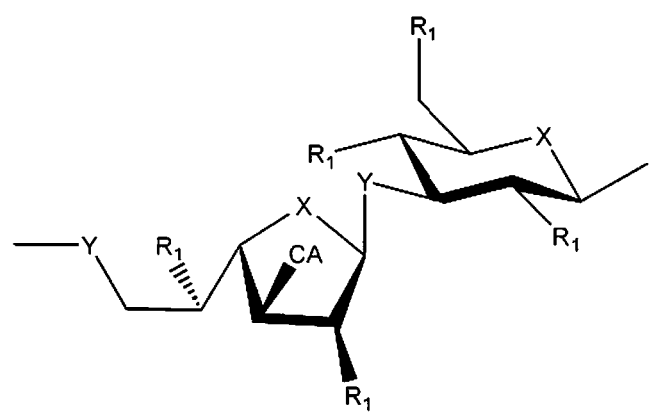

Carbon atom signals shifted to low field indicated substitutions on C-6 and C-3 of β-Galf (radical A, δ 71.90 and δ 84.96) and substitutions on C-3 of β-D-Glcp (radical B, δ 82.44). The sequence of the radicals in the repetitious unit was determined by ROESY experiments. Strong NOE contacts between the radicals were found between the protons A1 (δ 5.315) and B3 (δ 3.663), and B1(δ 4.542) and A6a (δ 3.768) (FIG. 2). Thus the structure of the repetitious unit of the isolated polysaccharide was as depicted in FIG. 3.

EXAMPLE 4

ELISA Studies

ELISA experiments were carried out by customary methods as described previously (Theilacker, C., et al., Infect. Immun. 74, 2006). Briefly, microtiter plates were coated with various carbohydrate antigens derived from *E. faecalis* (10 pg/ml in 0.04 M phosphate buffer, pH 7.0), and left at 4° C. for 18 hours. Washing steps were carried out using PBS containing 0.05% Tween 20. The plates were blocked with 3% skimmed milk in PBS-0.02% sodium azide at 37° C. for 2 hours. The secondary antibody used was a goat anti-rabbit IgG alkalinephosphatase conjugate (Sigma), diluted to 1:1000, with p-nitrophenyl phosphate being used as substrate (Sigma). After incubation at 37° C. for 60 minutes, absorption was measured at 405 nm.

EXAMPLE 5

Opsonophagocytosis Assay

An opsonophagocytosis assay was performed as described previously (Theilacker, C., et al., Infect. Immun. 74, 2006). Baby rabbit serum (Cedarlane Laboratories, Hornby, Ontario, Canada) absorbed with the target bacterial strain was used as complement source. The opsonic activity of the immune sera was compared to that of the controls containing normal rabbit serum. The immune serum was heat-inactivated at 56° C. for 30 minutes before use. Negative controls comprised sample tubes which either did not contain any polymorphonuclear leucocytes or any complement or any serum. The opsonic activity of the serum was calculated as follows: [1–(CFU immune serum at 90 min/CFU preimmune serum at 90 min)]×100. Opsonophagocytosis inhibition was studied by incubating antiserum in a concentration of 1:200 with from 0.08 to 100 μg/ml at 4° C. for 60 minutes. After incubation, the absorbed serum was added and the opsonophagocytosis assay was continued as described above. Without inhibition, all sera had a minimum opsonophagocytosis activity of >70% of the inoculum.

EXAMPLE 6

Immunochemical Characterization

Figure 4:
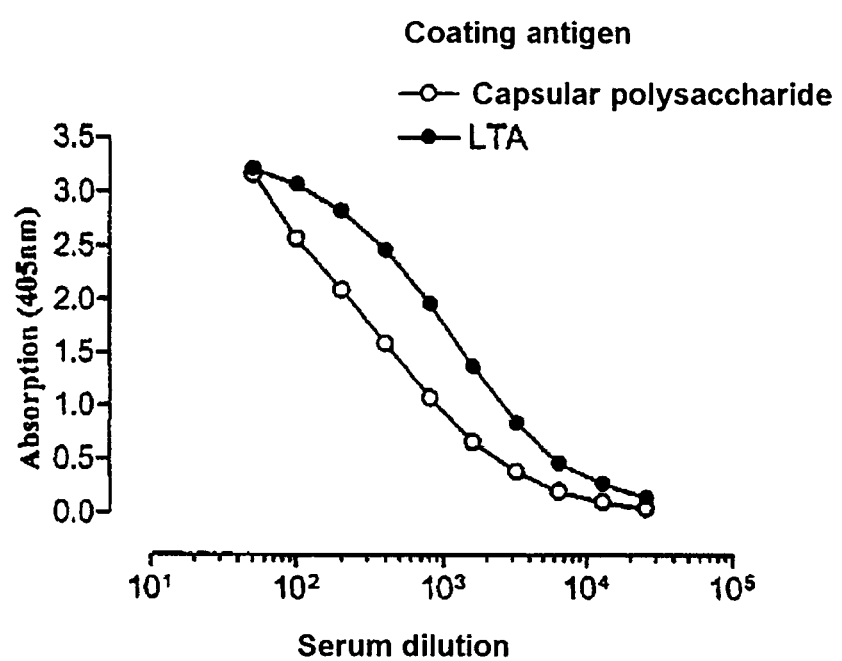
Figure 5:
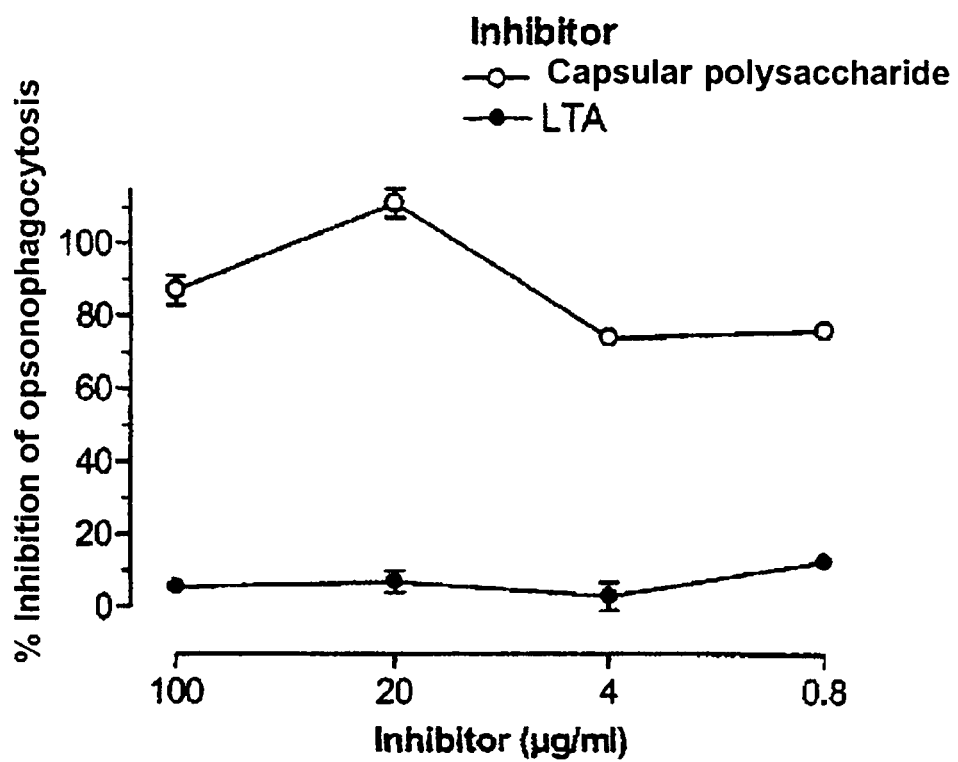

Serum against bacteria cells of *E. faecalis* type 5 (Maekawa, S., et al., Microbiol. Immunol. 36:671-681, 1992) was reactive to the purified polysaccharide (FIG. 4). The antiserum also contained high levels of IgG antibodies to *E. faecalis* LTA (FIG. 4). Since anti-LTA antibodies mediate opsonophagocytosis of the *E. faecalis* strain 12030, we intended to determine the specificity of opsonizing antibodies for the *E. faecalis* type 5 strain. Purified LTA did not inhibit the opsonophagocytosis activity of anti-type 5 serum (FIG. 5), in agreement with the observation that there is little cross-reactivity of opsonizing antibodies between *E. faecalis* type 5 and *E. faecalis* 12030 (Hufnagel, M., et al., J. Clin. Microbiol. 42:2548-2557, 2004). However, the purified capsular polysaccharide was a potent inhibitor of opsonizing antibodies to type 5 (FIG. 5). Rabbit serum against purified LTA, which promotes opsonophagocytosis of strain 12030 in the opsonophagocytosis assay, was non-opsonizing against the type 5 strain, confirming the results from our inhibition studies (data not shown).

EXAMPLE 7

Antibodies to the two polysaccharides of type 2 and of type 5 were raised in rabbits: a female white New Zealand rabbit was immunized subcutaneously with 100 μg of purified polysaccharide of type 2 and type 5 which had been suspended in complete Freund's adjuvant, and was then immunized with the same dose of polysaccharide suspended in incomplete Freund's adjuvant seven days later, and thereafter with 10 μg booster doses every three days for the following week.

Figure 6:
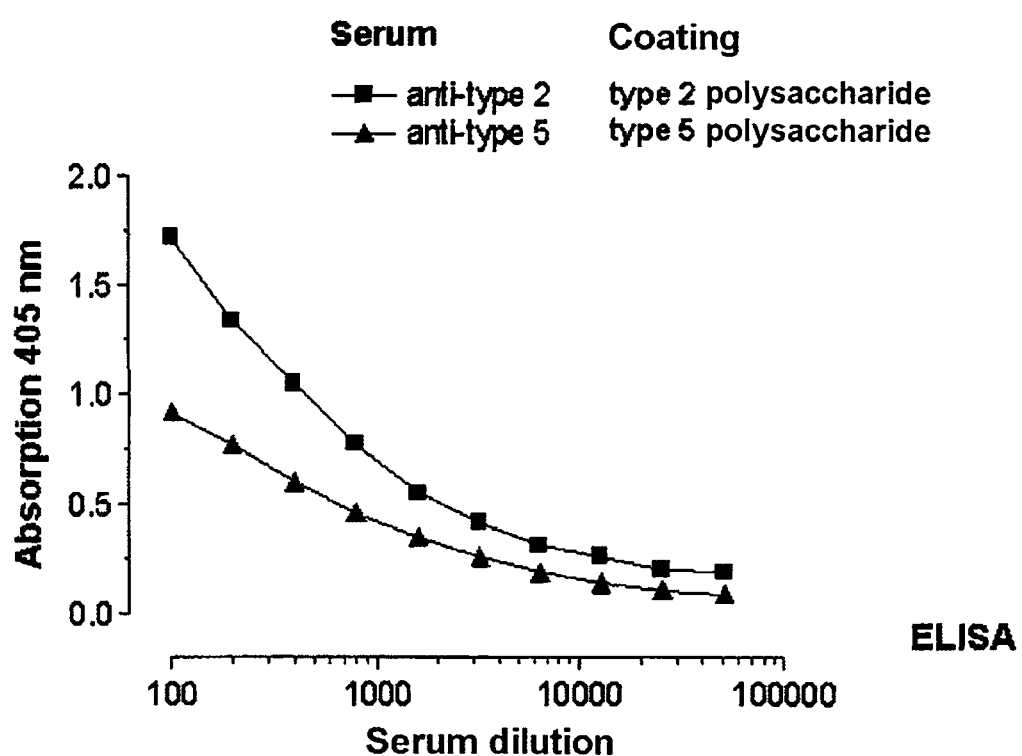
FIG. 6 depicts the binding of antibodies generated in rabbits to capsular polysaccharide of *E. faecalis* type 2 and type 5 to the corresponding purified antigen.

The polysaccharides were obtained by the method described under 2d). In each case two rabbits were used for immunization and the antiserum was subsequently obtained from the rabbits. The antisera obtained from the rabbits were studied in an ELISA. To this end, both the polysaccharide of type 2 and the polysaccharide of type 5 were bound to the microtiter plates. Surprisingly, antibodies were found to be produced both against purified polysaccharide of type 5 and against polysaccharide of type 2. This demonstrated that the antigen is immunogenic, a fact that was not necessarily expected in view of the fact that it is a "T cell-independent" antigen. Production of the antibodies is depicted in FIG. 6.

EXAMPLE 8

Opsonophagocytic Assay

This in vitro assay involved combining granulocytes, antiserum and bacteria and testing whether it was possible to kill the *Enterococcus faecalis* bacteria by the antibodies generated. The exact conditions of the assay mixture were as follows: fresh whole blood was obtained from healthy donors and admixed with a heparin dextran buffer. The white blood cells were then purified and adjusted to a defined number ($5 \times 10^6$ cells/ml). The bacteria to be studied were removed by centrifugation from a culture at average logarithmic growth and adjusted spectrophotometrically likewise to $5 \times 10^6$ cells/ml. The complement source used was lyophilized baby rabbit serum diluted 1:15 with cell culture medium and absorbed with the target bacteria strain in order to remove existing antibodies to the *Enterococcus* strain used. The rabbit serum was likewise diluted with cell culture medium in accordance with the experimental set up. For the experiment, in each case 100 μl of the bacterial suspension, 100 μl of leucocytes (bacteria: leucocytes ratio of 1:1), 100 μl of the complement source and 100 μl of the corresponding antibody dilution were mixed. The initial bacterial count was determined by dilution and plating out, and the experimental mixture was then incubated in an end over end rotator at 37° C. for 90 minutes. At the end of the experiment, the bacteria in the experimental mixture were likewise diluted again and plated out, and the number of colonies was counted on the next day. The reduction of the bacterial count between inoculum and the bacterial count at the end of the experiment was expressed as opsonophagocytosis-mediated killing in percent. This value represents the best surrogate marker for a protective immuno response to bacterial infectious pathogens.

Figure 7:
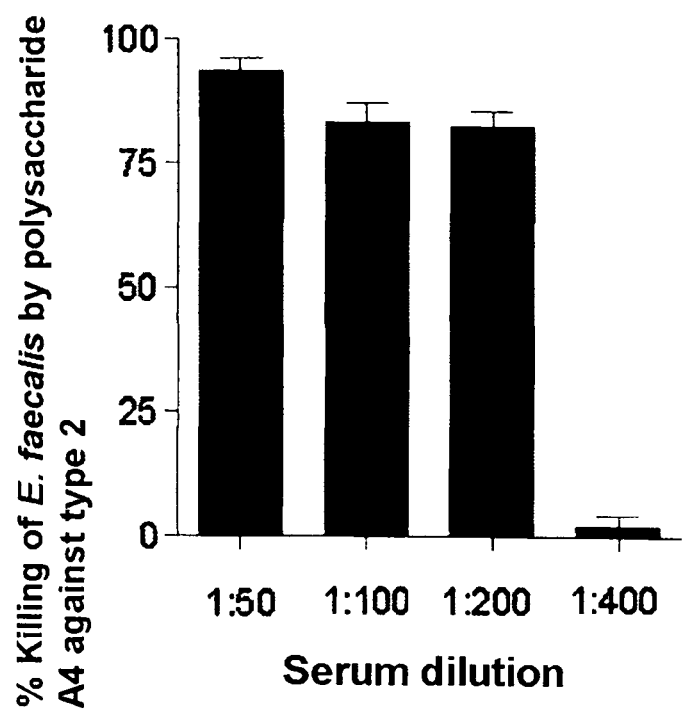
FIG. 7 depicts the determination of curing by opsonophagocytosis of *E. faecalis* type 2, which were produced against the purified antiserum. The values clearly demonstrate that protective antibodies were produced in rabbits, which resulted in the in vitro assay to destroy the bacteria.

The results of the experiment are depicted in FIG. 7. They demonstrate that serum dilutions of from 1:50 to 1:200 result in a marked killing of approx. 80%, while this effect is lost with further dilutions of the serum. This indicates that higher antibody titers to this antigen represent a protection of the organism from infection with *E. faecalis*.

The invention claimed is:

1. A vaccine comprising an isolated immunogenic *Enterococcus faecalis* antigen and an immunologically effective amount of an adjuvant, wherein the isolated antigen consists of, or consists essentially of, one or more units of Formula I:

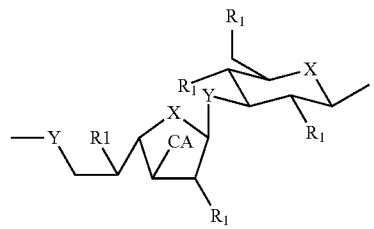

wherein $R_1$ is OH, X is O, Y is O and CA is lactyl.

2. The vaccine of claim 1, wherein the isolated antigen consists of two sugars, wherein the two sugars are in the D configuration.

3. The vaccine of claim 1, wherein the isolated antigen consists of one or more units of the following formula:

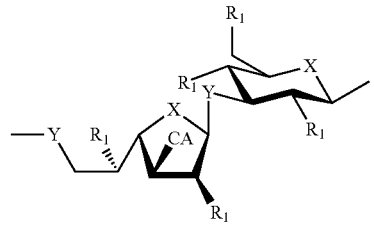

wherein $R_1$ is OH, X is O, Y is O and CA is lactyl.

4. The vaccine of claim 1, wherein the isolated antigen has a molecular weight of approx, 1000-200000 Da.

5. The vaccine of claim 1, wherein the isolated antigen consists of at least 5 units of Formula I per molecule.

6. The vaccine of claim 1, wherein the isolated antigen is bound to a support.

7. The vaccine of claim 1, wherein the binding to the support is covalent binding.

8. The vaccine of claim 1 wherein the isolated antigen consists of one or more units

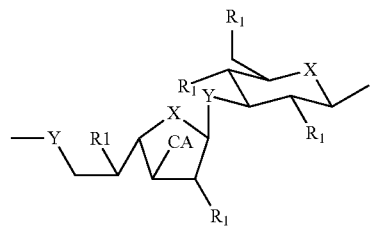

of Formula I:
wherein $R_1$ is OH, X is O, Y is O and CA is lactyl.

9. The vaccine of claim 1, wherein the isolated antigen consists essentially of one or more units of Formula I:

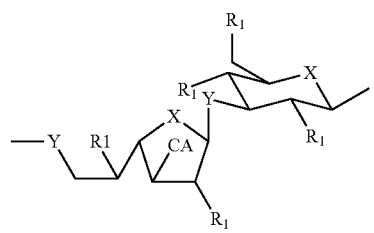

wherein $R_1$ is OH, X is O, Y is O and CA is lactyl.

* * * * *

UNITED STATES PATENT AND TRADEMARK OFFICE
CERTIFICATE OF CORRECTION

PATENT NO. : 9,796,744 B2  
APPLICATION NO. : 12/514653  
DATED : October 24, 2017  
INVENTOR(S) : Johannes Hübner et al.

Page 1 of 1

It is certified that error appears in the above-identified patent and that said Letters Patent is hereby corrected as shown below:

In the Specification

Column 10,
Lines 56-57, "DRX Advance" should read -- DRX Avance --.

Signed and Sealed this
Nineteenth Day of June, 2018

Andrei Iancu
*Director of the United States Patent and Trademark Office*